United States Patent [19]

Schaerffenberg et al.

[11] Patent Number: 4,751,082

[45] Date of Patent: Jun. 14, 1988

[54] INSECTICIDE AND METHOD FOR ITS DISTRIBUTION

[76] Inventors: Bruno Schaerffenberg, Zinzendorfgasse 21; Ilse Ramisch, Maiffredygasse 11, both of Graz, Austria, A-8010

[21] Appl. No.: 898,862

[22] Filed: Aug. 20, 1986

Related U.S. Application Data

[63] Continuation of Ser. No. 724,803, Apr. 19, 1985, abandoned, which is a continuation of Ser. No. 194,864, Oct. 7, 1980, abandoned, which is a continuation of Ser. No. 887,890, Mar. 20, 1978, abandoned, which is a continuation of Ser. No. 709,892, Jul. 29, 1976, abandoned.

[51] Int. Cl.$^4$ ...................... A01N 29/12; A01N 63/00
[52] U.S. Cl. ........................................ 424/93; 514/748
[58] Field of Search ........................... 424/93; 514/748

[56] References Cited

U.S. PATENT DOCUMENTS 3,013,946  12/1961  Lumb et al. ............................ 195/54
3,337,395   8/1967  Page ...................................... 424/93

FOREIGN PATENT DOCUMENTS 239595  8/1964  Austria .
262693  6/1968  Austria .

OTHER PUBLICATIONS

Chemical Week, Apr. 12, 1969, p. 57.
Chemical Week, Apr. 12, 1969, pp. 44, 48, 52, 60 & 65.
Chemical Week, Apr. 26, 1969, pp. 47 & 48.

*Primary Examiner*—Allen J. Robinson
*Attorney, Agent, or Firm*—Marmorek, Guttman Rubenstein

[57] ABSTRACT

A new method for controlling insects on plants is provided which comprises applying a composition comprising a chemical insecticide an an insecto-pathogenic fungus product which had been cultured on a substrate such as bran, whole meal, oatmeal and the like. The insecticidal compositions contain a combination of chemical insecticide and an insecto-pathogenic fungus.

5 Claims, No Drawings

INSECTICIDE AND METHOD FOR ITS DISTRIBUTION

This is a continuation of Ser. No. 724,803, filed Apr. 19, 1985, now abandoned, which is a continuation of Ser. No. 194,864, filed Oct. 7, 1980, now abandoned, which is a continuation of Ser. No. 887,890, filed Mar. 20, 1978, now abandoned, which is a continuation of Ser. No. 709,892, filed July 29, 1976, now abandoned.

The invention described in the following concerns a method of pest control by spraying on or powdering on a pesticide which is a combination of micro organisms and chemical insecticides, and an agent for the application of this method.

In the beginning of the forties the first insecticides on a chemical base were used in agriculture on a large scale. It was especially DDT which proved to be successful. Unfortunately symptoms of resistance against this agent showed up very soon. In the fifties the common housefly became resistant to DDT. Later on, other harmful insects, such as the potatoe beetle, the blossom rape beetle (*meligethes aeneus*) and the beet root weevil (*bothynoderes punctiventris*) became resistant to DDT, too. However, the agent was not only used in agriculture, but was applied almost universally. Clothings and a further series of commodity articles, packing material, cosmetics, etc., were preserved by means of DDT.

It is true that at the beginning small amounts of the agent were sufficient. However, in the fifties, the above mentioned symptoms of resistance necessitated an increase of the chemical base of the insecticide; the agents were more heavily chlorinated and the chlorinated insecticides Chlordane Heptachlor, Methoxychlor, Aldrin, Dieldrin and Lindan were developed. Very soon symptoms of resistance showed up against the phosphoric esters too, which had been developped later on.

As a consequence of this development more and more concentrated bases were used. This, however, entailed symptoms of poisoning in warm-bloods. Thus the insecticides on a chemical base began to show as dangerous neurotoxins and as cumulating agents causing damages of liver and heart and being cumulated in the adipose tissue. This not only in men, but also in domestic animals, the insecticides thus being re-fed to men via the nourishment.

Efforts to counteract the resistance by combining insecticides with different chemical bases remained without success. In any case the symptoms of poisoning did not disappear.

All attempts to counteract the resistance proved to be a failure. New chemical insecticides were developed continually, thus entailing an avalanchelike development of new agents, which—quite apart from the harmful effects—consumed much time and money.

We must realize that we cannot go on developing new insecticides interminately.

Therefore it is an urgent problem to develop methods of pest control which are harmless and not subject to phenomena of resistance.

It is well known that pesticides can be prepared from a mixture of micro organisms of the genus bacillus with synthetic pyrethroid insecticides. The action of pesticides of this kind is based on a synergistic effect, which has the disadvantage that the pests get resistant to the agent after some time.

About ten years ago a new insecticide on a biological base was developed by an Austrian research team. This insecticide is an agent made up of fungi of the classical muscardine type, such as *Beauveria bassiana, Beauveria tenella, Paecilomyces farinosus* and *Metarrhizium anisopliae*. The fungi act in an insecto-pathogenic way, i.e. the dried and comminuted material of fungi as well as the spores have infectious qualities. However, the dried material of fungi is richer in enzymes and toxic compounds.

The development of pest control on a biological base presented a method which was absolutely harmless to warm-bloods. It was proved that no symptoms of poisoning turned up. However, it was difficult to culture sufficient quantities of the fungi. It is true that with the use of insecto-pathogenic fungi np symptoms of resistance showed up, however, the mortality rate in insects was not sufficiently high. Therefore attempts were made to use the fungi in combination with bacilli. Thus e.g. *Beauveria bassiana* was used against the corn weevil in combination with the *Bacillus thuriengiensis*. For the control of potatoe beetles and greenflies *Beauveria bassiana* was combined with *Metarrhizium anisopliae* on the one hand and *Paecilomyces farinosus* with *Metarrhizium anisopliae* on the other hand.

There exists a series of insects with a special power of resistance to chemical insecticides as well as insecticides on a biological base. Thus it is almost impossible till now to get the potatoe beetle under control. In the United States a special procedure on a biological base with the aid of ladybird beetles had to be used.

The invention on hand presents the development of a new method, based on the combination of chemical insecticides and insecto-pathogenic fungi. The method according to the invention consists in the combination of a chemical insecticide with an insecto-pathogenic fungus cultured on substrates such as bran, whole meal, oat meal and the like.

The method according to the invention may be carried out in such a way as to infect the cultures at first with the chemical insecticide in order to achieve a weakening of the pest; after that the pest is destroyed by application of the mycelium. However, it is also possible to prepare a mixture of the chemical insecticide and the mycelium and to apply this mixture.

The pest control agent according to the invention consists of preferably 0.2–2 parts by weight of mycelium and 0.01–0.0001 parts by weight of insecticide. It has proved successful to spray on a solution of the agent according to the invention as well as to powder it on in its solid form. In the first case the usual solution is prepared with water, to which wetting agents are added. In the second case the agent according to the invention is mixed with powdered talc and dusted on the cultures. A combined application, i.e. dusting on one of the components in its solid form and spraying on a solution of the other component is also possible within the framework of the present invention.

According to the invention almost any chemical insecticide developed till now may be used. Thus e.g. the chlorinated aromatic compounds, such as DDT, benzene hexachloride, Chlordan, Metoxychlor, Heptachlor, Dieldrin, Aldrin, Endrin, the phosphoric esters, such as Phosdrin, Metasystox, Birlane, E 605 and Gusathion.

Examples for insecto-pathogenic fungi are especially those of the class of phycomycetes, such as *Entomophtora spaerosperma, Empusa muscae, Empusa aulicae* as well as those of the class of ascomycetes, such as *Beauv-*

*eria bassiana, Beauveria tenella, Paecilomyces fumosoroseus, Paecilomyces farinosus* and *Metarrhizium anisopliae.*

By the combination of micro organism or fungus, resp., with chemical insecticides a potentiation of the initial effect is brought about. This is not due to a synergism as it is the case with the combination of chemical insecticides or the combination of bacilli and chemical insecticides, resp., but rather to an effect of stimulation.

With the use of a subtle or reduced base of an insecticide a weakening of the treated insect is to be observed, which promotes the infection by means of the micro organism. The weakening of the insect is brought about by the fact that the hemocytes are either pathologically changed or directly destroyed by the insecticide, thus blocking phagocytosis. Phagocytosis is the most important defensive mechanism of an affected insect against the intruding micro organism. In the course of this process the hemocytes encircle the hyphae which have penetrated into the body cavity and dissolve them. This mechanism is hampered due to the weakening by means of the insecticide which destroys the hemocyte-system, thus preventing the hemocytes from intercepting the fungus. In addition to that a further working mechanism supports the effect of the micro organism according to the invention, i.e. the fact that pathogenic bacteria, cocci or rod-shaped bacilli from the intestine penetrate into the hemolymph after the destruction of the hemocytes, thus entailing septicemia of the pest.

The agent according to the invention is not only effective against non-resistant pests but also against pests which have already got resistant, and this with a considerably smaller and already harmless dose of chemical insecticide. It is also remarkable that the present invention may be applied to all stages of development of the pest, e.g. the pupa, the larva, as well as to hatched insects, with equally good results.

The cultures of fungi for the mycelium which is used according to the invention may be prepared either according to the submersion process or according to the surface process. The first method requires a considerable expenditure of apparatus and careful handling, especially with regard to the preparation of the nutritive substrate and with regard to aeration as well as maintenance of the optimal conditions concerning temperature and pA-value.

According to the surface process the insecto-pathogenic fungi are fermented on porous materials, such as bran, whole meal, oat flakes, etc., mixed with water. The preparation of fungi-bran is described in Ullmann, Enzyklopaedie der techn. Chemie, 1956, volume 7. pp. 407–408.

The fermentation of fungi of the muscardine type and the preparation of the mycelium are described in detail in the Austrian patent specification OPS No. 262693. The use of bran, whole meal, oat flakes or bread crumbs enables the culture of virulent pathogenic agents of the fungus. The mentioned substrates are not only rich in vitamins acting as growth factors but also—like the destroyed pests—in phosphate, enzymes (factors of infection) and amino-acids as metabolic factors, thus enabling the culture of virulent insecto-pathogenic fungi in considerable quantities and the mass production of their spores at a large technical scale in culture tanks. Not only the spores, but the whole fungus, i.e. the nutritive substrate turned into fungus material, is obtained. Thus the whole culture is regained and can be used for the extirpation of the pests.

At first a pre-culture for the inoculation of the main culture is prepared. The substrate is mixed with water and sterilised. The nutritive substrate is agitated to obtain a fluffy mass with a large surface. The containers for the cultures are to be chosen with a suitable capacity in order to ensure a sufficient air space above the culture. Then the culture is inoculated with the spores. The inoculated culture is fermented over a period of several days at temperatures which are optimal for the respective fungus (between 26° and 28° C.). The substrate changes into a homogenous mass of fungi and spores, which is used for the inoculation of larger cultures. Inoculation and fermentation of the cultures at a large technical scale are carried out in the same way as is done with the pre-culture, After fermentation the prepared fungus material is dried and pulverized.

The produce is either mixed with the usual extenders or processed into a solution containing wetting materials. It is essential that the entire nutritive substrate is turned into mycelium. According to the invention the mycelium is used in combination with a conventional insecticide.

The invention on hand is illustrated by means of control tests which are set out in the following tables. These tests are laboratory tests, for which the larva 1 of the potatoe beetle, the potatoe beetle itself and the cabbage aphid were put into preserving jars together with watered potatoe haulm. In each jar there were 50 test insects. The tests were carried out by treating the pests with a mixture of DDT and *Beauveria bassiana.* For the control tests they were treated only with either DDT or *Beauveria bassiana.*

| days | mortality rate if treated with 0.008% by weight of DDT | mortality rate if treated with 0.5% by weight of *Beauveria bassiana* | mortality rate if treated with 0.008% by weight of DDT and 0.5% by weight of *Beauveria bassiana* |
|---|---|---|---|
| | | (I) larve 1 of the potatoe beetle | |
| 2 | 10 | 0 | 49 |
| 4 | 15 | 3 | 50 |
| 6 | 15 | 10 | 54 |
| 8 | 31 | 32 | 65 |
| 10 | 40 | 35 | 65 |
| 12 | 40 | 40 | 76 |
| | | (II) potatoe beetle | |
| 2 | 2 | 0 | 8 |
| 4 | 2 | 0 | 15 |
| 6 | 2 | 0 | 20 |
| 8 | 4 | 0 | 32 |
| 10 | 8 | 0 | 45 |
| 12 | 10 | 0 | 50 |
| 14 | 10 | 0 | 72 |
| | | (III) Cabbage aphid | |
| 2 | 12 | 10 | 92 |
| 4 | 15 | 12 | 98 |
| 6 | 18 | 15 | 100 |
| 8 | 19 | 18 | |
| 10 | 22 | 20 | |
| 12 | 30 | 27 | |

Further tests were carried out with combinations of *Beauveria bassiana, Metarrhizium anisopliae* and *Paecilomyces farinosus* with DDT, E605, Phosdrin and Metasystox. The test insects were potatoe beetles, turnip sawflies, several kinds of greenflies, cabbage caterpillars, small spruce sawflies, large brown weevils, cabbage moths and bark beetles.

The values given in tables I to III illustrate the effect of the invention on one of the most persistant pests.

Correspondingly better results were achieved with less persistant insects.

With the combination of the fungus with E605 at a concentration of 0.0001% a mortality rate of 65% was achieved at the 6th day and a mortality rate of 89% after 11 days. The control values for the use of either E605 or fungus were 31.2% and 43%. In the case of the turnip sawfly, the greenfly, the bean aphid and the peach greenfly (*Myzodes persicae*) a mortality rate of 100% was achieved already after three days with a combination of 0.001% DDT end 0.08% fungus, thanks to the invention.

The invention at issue will now be illustrated by some examples for the application of the method in outdoor tests.

EXAMPLE 1

A field of 1 ha (2.4711 acres) contaminated with potatoe beetles was divided into four areas of equal dimensions. One quarter of the field was sprayed with an aqueous solution of 2 g DDT/100 ml water. The second part of the field was treated with a mixture of 1 g DDT and 1 g E605 in 100 ml of water. The third part was sprayed with an aqueous solution of *Beauveria bassiana* at a concentration of 0.6 g fungus/100 ml water. The last part was sprayed with the agent according to the invention at a concentration of 0.1 g. *Beauveria bassiana* and 0.0005 g DDT. Each part was treated with 120 l of pest control agent. The mortality rates were ascertained for one square meter of each of the four parts:

| | |
|---|---|
| DDT | 2% |
| DDT + E605 | 7% |
| *Beauveria bassiana* | 28% |
| DDT + *Beauveria bassiana* | 68% |

Spraying was repeated on the following day. With the mixture of *Beauveria bassiana* and DDT the mortality rate was increased to 85%, whereas no improvement was achieved by the other three sprayings.

EXAMPLE 2

Similar to example 1 with the difference that each part was powdered with 12 kg of a mixture of the pest control agent with powdered talc.

| | | |
|---|---|---|
| (A) | 2 g DDT/100 g powdered talc mortality rate | 1.8% |
| (B) | 1 g DDT + 1 g E605/10 g powdered talc mortality rate | 8.4% |
| (C) | 0.8 g *Beauveria bassiana*/10 g powdered talc mortality rate | 27.3% |
| (D) | 0.5 g *Beauveria bassiana* + 0.01 g DDT/10 g powdered talc mortality rate | 65% |

A second powdering resulted in an increase of the mortality rate to 83%.

EXAMPLES 3 TO 8

Further mixtures of insecto-pathogenic fungi and chemical insecticides were prepared and the mortality rates were ascertained. The results are given in the following table:

| micro organism | insecticide | proportion of the quantity of micro organism and the quantity of insecticide/ 100 ml water | mortality rate |
|---|---|---|---|
| *Paecilomyces farinosus* | Phosdrin | 0.6:0.006 | 70:100% |
| *Beauveria bassiana* | DDT | 0.5:0.005 | 80:100% |
| *Beauveria bassiana* | HCH | 0.5:0.005 | 80:100% |
| *Metarrhizium anisopliae* | DDT | 0.5:0.005 | 80:100% |
| *Bacillus thueriengiensis* | DDT | 1:0.05 | 60:100% |

We claim:

1. An insecticidal composition for killing pests having hemolytic systems, comprising
a combination of DDT and a mycelium of *Beauveria bassiana* fungus to produce an effect of stimulation in said pests, and
an agriculturally acceptable carrier,
said DDT being in the range of about 0.001 to about 0.008 percent by weight and sufficient to impair the hemolytic systems of said pests, thereby weakening said pests by affecting the antimicrobial defenses thereof,
said mycelium being in the range of about 0.08 to about 0.5 percent by weight at a level suitable for killing said pests having impaired hemolytic systems.

2. The insecticidal composition of claim 1, wherein said DDT is about 0.008 percent by weight and said mycelium is about 0.5 percent by weight.

3. An insecticidal composition of claim 1, wherein said carrier is selected from the group consisting of water, talc, bran, whole meal, oat flakes and bread crumbs.

4. An insecticidal composition for killing pests having hemolytic systems, comprising
a combination of 0.0005 grams of DDT per 100 milliliter of water and 0.1 gram of a mycelium of *Beauveria bassiana* fungus per 100 milliliter of water to produce an effect of stimulation in said pests, whereby said DDT impairs the hemolytic systems of said pests and said mycelium kills said pests having impaired hemolytic systems.

5. An insecticidal composition for killing pests having hemolytic systems, comprising
a combination of 0.01 gram of DDT per 10 grams of powdered talc and 0.5 gram of a mycelium of *Beauveria bassiana* fungus per ten grams of powdered talc, whereby said DDT impairs the hemolytic systems of said pests and said mycelium kills said pests having impaired hemolytic systems.

* * * * *